| (12) | United States Patent | (10) Patent No.: | US 9,597,115 B2 |
|---|---|---|---|
| | Zhou | (45) Date of Patent: | Mar. 21, 2017 |

(54) RING SEALING APPARATUS FOR TROCAR AND TROCAR

(75) Inventor: Xing Zhou, Guangzhou (CN)

(73) Assignee: GUANGZHOU T. K. MEDICAL INSTRUMENT CO. LTD., Guangzhou, Guangdong (CN)

( * ) Notice: Subject to any disclaimer, the term of this patent is extended or adjusted under 35 U.S.C. 154(b) by 952 days.

(21) Appl. No.: 13/993,917

(22) PCT Filed: Dec. 11, 2011

(86) PCT No.: PCT/CN2011/083796
§ 371 (c)(1),
(2), (4) Date: Jun. 13, 2013

(87) PCT Pub. No.: WO2012/083798
PCT Pub. Date: Jun. 28, 2012

(65) Prior Publication Data
US 2013/0267981 A1 Oct. 10, 2013

(30) Foreign Application Priority Data
Dec. 21, 2010 (CN) .......................... 2010 1 0599090

(51) Int. Cl.
*A61B 17/34* (2006.01)

(52) U.S. Cl.
CPC ...... *A61B 17/3498* (2013.01); *A61B 17/3462* (2013.01); *A61B 2017/349* (2013.01); *A61B 2017/3464* (2013.01)

(58) Field of Classification Search
CPC . A61B 17/3498; A61B 17/34; A61B 17/3462; A61M 2039/0626; A61M 2039/0633
(Continued)

(56) References Cited

U.S. PATENT DOCUMENTS

| 5,197,955 A | | 3/1993 | Stephens et al. |
| 5,263,944 A | * | 11/1993 | Vidal ................ A61B 17/3462 604/167.01 |

(Continued)

FOREIGN PATENT DOCUMENTS

| CN | 101138662 A | 3/2008 |
| CN | 101474089 A | 7/2009 |

(Continued)

OTHER PUBLICATIONS

Zho, Communication Rules 70(2) and 70a(2) EPC, EP11851107.0, Oct. 21, 2014, 1 pg.

(Continued)

*Primary Examiner* — Julie A Szpira
(74) *Attorney, Agent, or Firm* — Morgan, Lewis & Bockius LLP (57) ABSTRACT

A rotary structure having a large upper part, a small middle part and a large lower part is formed between guiding blocks (11) of a guiding mechanism (1). A positioning groove (10) is disposed at the wasp-waist of the guiding block (11). The bottom of a sealing ring (3) is embedded in the positioning groove (10) to surround the guiding block (11). When a surgical instrument is inserted, the sealing ring (3) confined within the positioning groove (10) extends out of the gap between the guiding blocks (11) to surround the instrument. The contact area between the sealing ring (3) and the instrument provides a guiding function to different forms of surgical instrument and transforms a "soft-hard" friction area between the sealing ring (3) and the instrument into a "hard-hard" friction area between a plastic guiding surface of the guiding blocks (11) and an outer metal sheath of the instrument.

21 Claims, 7 Drawing Sheets

(58) Field of Classification Search
USPC ........ 606/185; 604/167.01–167.06; 277/603, 277/562, 644; 600/185, 184
See application file for complete search history.

(56) References Cited

U.S. PATENT DOCUMENTS

| | | | | |
|---|---|---|---|---|
| 5,342,315 | A * | 8/1994 | Rowe | A61B 17/3462 604/167.06 |
| 5,391,153 | A * | 2/1995 | Haber | A61B 17/3462 604/167.01 |
| 5,411,483 | A * | 5/1995 | Loomas | A61B 17/3462 604/167.06 |
| 5,542,931 | A | 8/1996 | Gravener et al. | |
| 5,603,702 | A * | 2/1997 | Smith | A61B 17/3462 251/149.1 |
| 5,628,732 | A * | 5/1997 | Antoon, Jr. | A61B 17/3462 604/167.06 |
| 5,720,759 | A * | 2/1998 | Green | A61B 17/3462 604/165.01 |
| 5,814,026 | A | 9/1998 | Yoon | |
| 5,989,224 | A * | 11/1999 | Exline | A61B 17/3462 604/167.02 |
| 6,482,181 | B1 * | 11/2002 | Racenet | A61B 17/3462 137/874 |
| 6,702,787 | B2 * | 3/2004 | Pasqualucci | A61B 17/34 604/158 |
| 7,011,314 | B2 * | 3/2006 | McFarlane | A61B 17/3462 277/626 |
| 8,100,929 | B2 * | 1/2012 | Franer | A61B 17/3462 277/626 |
| 2004/0068232 | A1 * | 4/2004 | Hart | A61B 17/3462 604/167.06 |
| 2004/0106942 | A1 | 6/2004 | Taylor et al. | |
| 2008/0051739 | A1 * | 2/2008 | McFarlane | A61B 17/3462 604/278 |
| 2009/0192465 | A1 * | 7/2009 | Smith | A61B 17/3421 604/164.04 |
| 2009/0234293 | A1 * | 9/2009 | Albrecht | A61B 17/3421 604/167.02 |
| 2010/0010446 | A1 * | 1/2010 | Schweitzer | A61B 17/3498 604/167.01 |
| 2010/0022957 | A1 * | 1/2010 | Sauer | A61B 17/3462 604/164.03 |
| 2011/0237901 | A1 * | 9/2011 | Duke | A61B 17/3462 600/208 |

FOREIGN PATENT DOCUMENTS

CN     101505665 A     8/2009
CN     202051787 U     11/2011

OTHER PUBLICATIONS

Zho, Invitation to file search results Rule 70b(1), EP11851107.0, May 11, 2015, 1 pg.
Zho, First Office Action, CN201010599090.2, Jan. 15, 2015, 11 pgs.
Zho, Extended European Search Report, EP11851107.0, Oct. 2, 2014, 6 pgs.
Xing Zhou, International Search Report, PCT/CN2011/083796, Mar. 1, 2012, 4 pgs.

* cited by examiner

RING SEALING APPARATUS FOR TROCAR AND TROCAR

CROSS REFERENCE TO RELATED APPLICATIONS

This Application is a United States National Stage Application filed under 35 U.S.C. §371 of PCT Patent Application Serial No. PCT/CN2011/083796 filed on Dec. 11, 2011, which claims the benefit of and priority to Chinese Patent Application No. 201010599090.2 filed on Dec. 21, 2010, both of which are hereby incorporated by reference in their entireties.

TECHNICAL FIELD

The disclosed implementations relate generally to a medical instrument, and in particular, to a sealing apparatus for a trocar used in a laparoscopic surgery and a trocar using the sealing apparatus.

BACKGROUND

A laparoscopic surgery is applied more and more widely. In order to avoid iatrogenic infection, the consumption of a disposable trocar used in the laparoscopic surgery is increasingly greater. The trend of simplifying the structure, reducing the cost, improving the performance on the basis of ensuring using performance has already become an improvement direction of the trocar.

In the prior art, the sealing of the trocar is formed by a radial sealing apparatus and an axial sealing apparatus.

A common axial sealing apparatus, namely, a check valve has many types. One type is a spring pressed check valve, forming sealing by a spring leaf pushing a flapper to oppress a silica gel sealing ring. The check valve is formed by the spring leaf, the flapper and the silica gel sealing ring. The spring leaf is made of stainless steel, and the flapper is made of medical plastics. The form of the axial sealing apparatus is usually used in a reusable trocar. In recent years, in order to adapt to the development requirement of the disposable trocar, a funnel-shaped silica gel sealing ring is developed. The funnel-shaped silica gel sealing ring has a straight through notch provided at the bottom of the funnel, and achieves the sealing effect by means of the contractility of the silica gel and the pressure formed by carbon dioxide pneumoperitoneum during use. The funnel-shaped silica gel sealing ring is generally widely used in the disposable trocar.

In the prior art, the radial sealing apparatus generally adopts a silica gel sealing ring of a funnel-shaped structure with a central hole, and the sealing ring easily leaks when a surgical instrument shakes, having a poor dynamic sealing effect. Particularly, when a 10 mm or 12 mm surgical instrument is inserted into a surgical instrument through hole of a sealing ring with the diameter being 4 mm, the resistance of the surgical instrument in reciprocating motion is large, which brings inconvenience to a surgical operation of a surgeon.

Surgical instruments have heads in different shapes. Particularly, a surgical instrument, such as a titanium clamp, having a V-shaped head splayed when being delivered to the abdominal cavity generally cannot pass through the sealing ring in the prior art, or may puncture the sealing ring in the prior art, thereby causing gas leakage. Another defect of the radial sealing apparatus in the prior art is that the type of the surgical instrument whose head has a groove or raised steps is easy to get stuck when the surgical instrument is removed, so the motion is not smooth.

Therefore, the radial sealing apparatus of the trocar in the prior art needs to be improved, so as to achieve the purpose of not only using a 10 mm surgical instrument on a trocar with the diameter being 10 mm, but also using surgical instruments with diameters between 5 mm and 10 mm; and not only using a 12 mm instrument on a trocar with the diameter being 12 mm, but also using surgical instruments with diameters between 5 mm and 12 mm, thereby being general. Meanwhile, the radial sealing apparatus of the improved trocar can be adapted to various surgical instruments in different shapes, thereby facilitating the insertion and removal of the instrument, with low resistance and smooth motion. Evidently, the sealing apparatus and the trocar in the prior art cannot satisfy the requirements, thus requiring improvement.

SUMMARY

The present invention is directed to a radial sealing apparatus used for a trocar and a trocar using the sealing apparatus, which are capable of using surgical instruments with diameters between 5 mm and 12 mm, thus having generality, desirable sealing effect, and low resistance.

The core of technical solutions of the present invention of lies in that:

The motion of an outer sheath of a surgical instrument in a radial sealing apparatus is mainly in contact with guiding blocks of a guiding mechanism, a rotary structure having a large upper part, a small middle part and a large lower part is formed between the guiding blocks, and a sealing ring is mounted in a positioning groove of the guiding block. The design minimizes the contact area between the surgical instrument and the sealing ring, which not only provides a guiding function when an instrument is inserted or removed, being applicable to all forms of insertion and removal of the surgical instrument; but also maximally transforms a "soft-hard" friction area between a silica gel sealing ring and the surgical instrument into a "hard-hard" friction area between plastic guiding blocks and an outer metal sheath of the surgical instrument, thereby greatly reducing the motion resistance of the surgical instrument in the sealing apparatus and the trocar.

The low-resistance general sealing apparatus of the present invention is implemented as follows.

A ring sealing apparatus for a trocar is provided. The sealing apparatus includes a guiding mechanism and a sealing ring, where the guiding mechanism includes a positioning groove mounted with a sealing ring and at least 2 guiding blocks; a rotary structure having a large upper part, a small middle part and a large lower part is formed between the guiding blocks; the positioning groove is disposed at the wasp-waist of the guiding block; the sealing ring is made of an elastic medical macromolecular material, and is provided with a surgical instrument through hole; and the sealing ring is mounted in the positioning groove.

Furthermore, the bottom of the sealing ring close to the surgical instrument through hole is placed between an upper edge and a lower edge of the positioning groove and is fixed together through a connection locking mechanism, thereby forming a sealing structure.

An angle α between the upper edge of the positioning groove and a perpendicular base of the positioning groove is between 90° and 30°, and optimally between 87° and 45°; and an angle β between the lower edge of the positioning groove and the vertical base of the positioning groove is between 90° and 30°, and optimally between 87° and 45°. After the upper edge of the positioning groove and the lower edge of the positioning groove are locked through the connection locking mechanism, the existence of the angles α and β has the effect of centripetal pressing on the sealing ring in the positioning groove, thereby enhancing the surrounding force of the sealing ring on the surgical instrument and forming a sealing effect.

A cone angle γ formed by the guiding block on the upper side of the guiding mechanism is between 180° and 20°, and optimally between 100° and 30°.

The guiding mechanism includes 4 guiding blocks; 2 guiding blocks whose area of a guiding surface is larger form a pair of main guiding sliders, the rest 2 guiding blocks whose area of a guiding surface is smaller form a pair of auxiliary guiding sliders, and the main guiding sliders and the auxiliary guiding sliders have different colors.

The part of the upper side of the sealing ring close to the edge includes a low-resistance buffer area easy to deform elastically.

Furthermore, the low-resistance buffer area of the sealing ring adopts a wrinkle structure.

The sealing ring is a sealing ring having a trapezoidal, V-shaped and H-shaped cross section; and the trapezoidal sealing ring is preferred.

Furthermore, when the sealing ring is a sealing ring having a trapezoidal cross section, the diameter $D_{31}$ of the surgical instrument through hole is between 1 mm and 5 mm, and optimally between 2.5 mm and 4.5 mm; the diameter $D_{32}$ of the bottom of trapezoidal sealing ring is between 3 mm and 40 mm, and optimally between 10 mm and 30 mm; and the thickness δ of the bottom of the trapezoidal sealing ring is between 0.05 mm and 5 mm, and optimally between 0.3 mm and 2 mm.

The sealing apparatus includes a dynamic connection mechanism.

Furthermore, the dynamic connection mechanism refers to an elastic low-resistance area that is formed by an elastic material, easily deforms under an external force and restores its shape after the external force of deformation is removed; or, the dynamic connection mechanism refers to a movable ball connection rotation mechanism or a shaft connection rotation mechanism.

The low-resistance area is a groove structure having a variable thickness.

The ball connection rotation mechanism includes a ball limit slot and a ball movable in the ball limit slot, and the ball can be movably mounted in the ball limit slot.

The shaft connection rotation mechanism includes a shaft limit slot and a shaft movable in the shaft limit slot, and the shaft can be movably mounted in the shaft limit slot.

The sealing apparatus includes a translation slider mechanism.

The translation slider mechanism includes a horizontal slider and a horizontal positioning plate, and the horizontal slider movable in the horizontal direction is placed on the horizontal positioning plate.

Furthermore, the horizontal slider includes a positioning groove mounted with a dynamic connection mechanism, a cover plate, and a fastener.

The connection locking mechanism connects the upper edge of the positioning groove and the lower edge of the positioning groove together fixedly through a concave-convex matching mechanism; or, the connection locking mechanism connects the upper edge of the positioning groove and the lower edge of the positioning groove together fixedly by adopting a heat seal or welding technology through a concave-convex matching structure; or, the connection locking mechanism connects the upper edge of the positioning groove and the lower edge of the positioning groove together fixedly by adopting a chemical binder through a concave-convex matching structure.

Ultra smooth material coating is arranged on the guiding surface of the guiding block. The ultra smooth material coating is generally made of a hydrophilic material, or may be made of a material with a self-lubricating function.

Furthermore, the medical flexible macromolecule material is selected from medical silica gel, medical rubber, medical polyurethane, medical latex and a combination thereof.

The guiding mechanism, the dynamic connection mechanism, the connection locking mechanism and the translation slider mechanism are made of medical macromolecular materials or medical metal materials that are selected from medical macromolecular materials such as medical PU, PP, PA, PE, PC and medical PTEF, or medical metal materials such as medical stainless steel, medical titanium and titanium alloy, medical TiNi Shape memory alloy and TiZrNb alloy.

The present invention further provides a trocar.

The trocar includes a ring sealing apparatus for a trocar according to the present invention.

Furthermore, the ring sealing apparatus for a trocar is mounted in a sheath of the trocar.

The radial sealing of the trocar adopts the ring sealing apparatus of the present invention, and the axial sealing adopts a funnel-shaped straight sealing ring.

The radial sealing of the trocar adopts the ring sealing apparatus of the present invention, and the axial sealing adopts a flipping-type sealing apparatus.

The radial sealing of the trocar adopts the ring sealing apparatus of the present invention, and the axial sealing adopts a spherical sealing apparatus.

In the prior art, a sealing ring of a trocar is generally made of a medical elastic material, and the common material is medical silica gel. The outer sheath of the surgical instrument is generally made of metal. When a surgical instrument moves in the medical silica gel, the frictional resistance is large, while the frictional resistance between the outer metal sheath of the surgical instrument and the plastics is small. The different of the present invention lies in that: the contact between the plastic guiding surface of the guiding block and the outer metal sheath of the surgical instrument is used to replace the contact between the silica gel sealing ring and the outer metal sheath of the surgical instrument, so as to reduce the contact area of the silica gel sealing ring that surrounds the surgical instrument as much as possible, thereby reducing the frictional resistance.

The rotary structure having a large upper part, a small middle part and a large lower part is formed between the guiding blocks of the guiding mechanism of the present invention, the positioning groove is disposed at the wasp-waist of the guiding block, and the bottom of the sealing ring is embedded in the positioning groove, so as to surround the guiding block from the outside. When the surgical instrument is inserted, the sealing ring confined within the positioning groove extends out of the gap between the guiding blocks to surround the surgical instrument to form sealing. The sealing apparatus of the present invention minimizes the contact area between the sealing ring and the surgical instrument, which not only provides a guiding function when the surgical instrument is inserted or removed, being applicable to all forms of insertion and removal of the surgical instrument; but also maximally transforming a "soft-hard" friction area between the sealing ring and the surgical instrument into a "hard-hard" friction area between the plastic guiding surface of the guiding block and the outer metal sheath of the surgical instrument, thereby minimizing the motion resistance of the surgical instrument in the sealing apparatus and the trocar. Meanwhile, the sealing apparatus and the trocar of the present invention are applicable to surgical instruments with diameters between 5 mm and 12 mm, with excellent sealing effect and low motion resistance.

Additionally, the lower guiding blocks of the guiding mechanism of the sealing apparatus of the present invention not only provide a guiding function, but also have the effect of preventing turnover of the sealing ring when the surgical instrument is withdrawn outward. The turnover of the sealing ring greatly increases the resistance when the surgical instrument is withdrawn, so the sealing apparatus of the present invention effectively avoids the turnover phenomenon.

By means of the sealing apparatus of the present invention, surgical instruments with diameters between 12 mm and 5 mm can freely insert in the sealing apparatus, while maintaining excellent dynamic sealing performance, thereby implementing the generality. The sealing apparatus and the trocar of the present invention may further implement free changing of the surgical instruments with diameters between 5 mm and 15 mm while maintaining low motion resistance.

BRIEF DESCRIPTION OF DRAWINGS

The aforementioned implementation of the invention as well as additional implementations will be more clearly understood as a result of the following detailed description of the various aspects of the invention when taken in conjunction with the drawings. Like reference numerals refer to corresponding parts throughout the several views of the drawings.

FIG. 1-1 is a schematic structural diagram of a general sealing ring in the prior art.

FIG. 1-2 is a schematic structural diagram of a sealing ring after the surgical instrument is inserted in FIG. 1-1.

Figure 11:
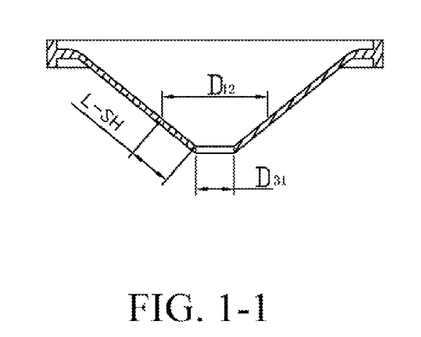
Figure 12:
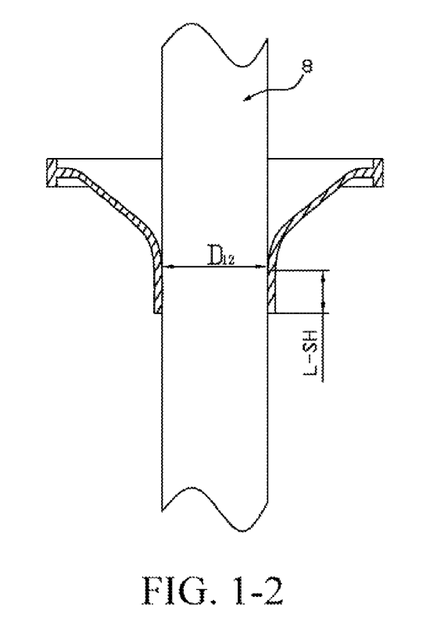

In FIG. 1-1 to FIG. 1-2, $D_{31}$ is the diameter of a surgical instrument through hole of the sealing ring, $D_{12}$ is the position of an arc with the diameter being 12 mm, and the L-SH represents the length of a "soft-hard" friction area formed between a silica gel sealing ring and an outer metal sheath of the surgical instrument after a 12 mm surgical instrument is inserted. In the prior art, for the general sealing ring, after the 12 mm surgical instrument 8 is inserted, the L-SH of the "soft-hard" friction area formed between the silica gel sealing ring and the outer metal sheath of the surgical instrument is long and the frictional resistance is large.

FIG. 2-1 is a schematic structural diagram of a 4-petal ring sealing apparatus according to the present invention.

FIG. 2-2 is an operation principle diagram of FIG. 2-1.

Figure 21:
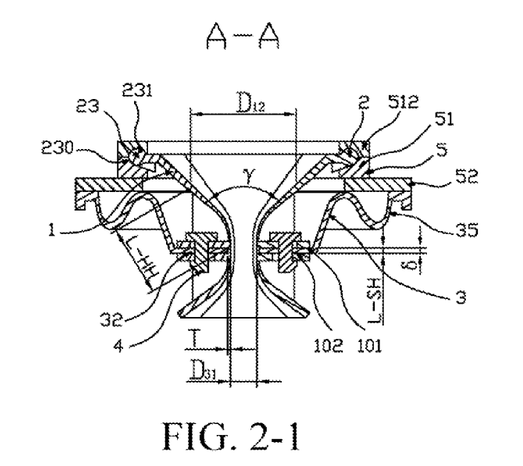
Figure 22:
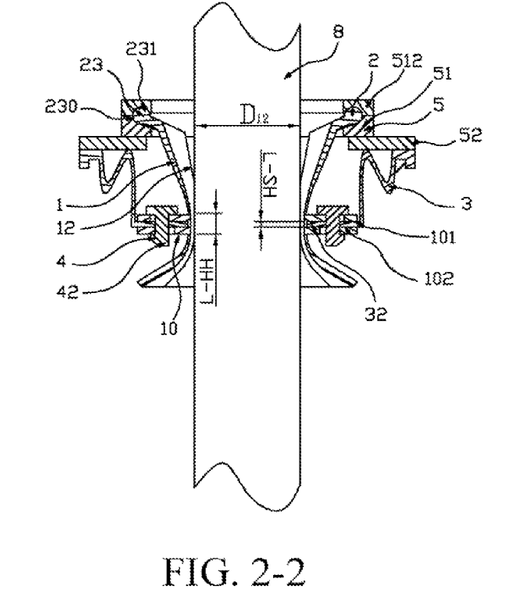
Figure 23:
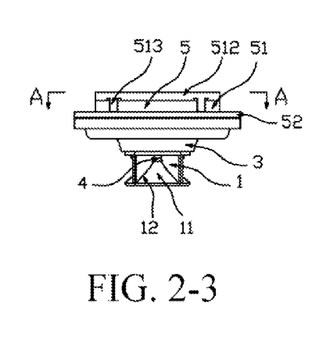
Figure 24:
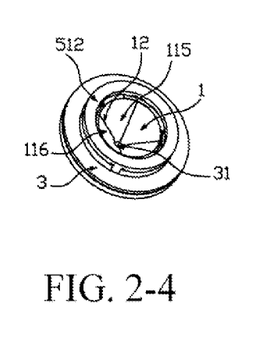
Figure 25:
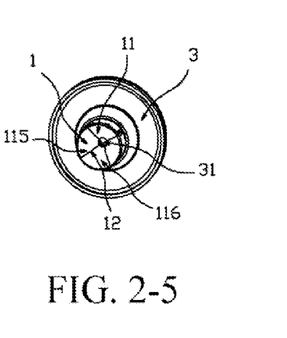
Figure 26:
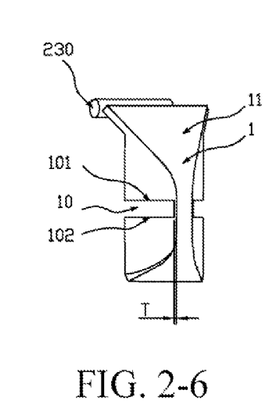
Figures 27, 28:
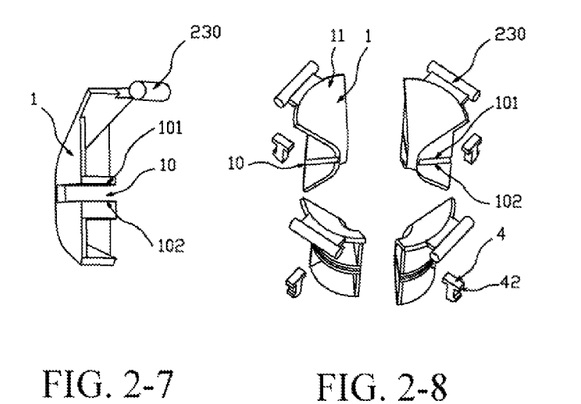

In FIG. 2-1 to FIG. 2-2, FIG. 2-1 is also an A-A sectional view of FIG. 2-3. $D_{31}$ is the diameter of a surgical instrument through hole 31 of the sealing ring, $D_{12}$ is the position of an arc with the diameter being 12 mm, and the L-SH represents the length of a "soft-hard" friction area formed between a silica gel sealing ring 3 and an outer metal sheath of the surgical instrument after a 12 mm surgical instrument 8 is inserted. L-HH represents the length of a "hard-hard" friction area formed between a plastic guiding surface and an outer metal sheath of the surgical instrument 8 after a 12 mm surgical instrument is inserted. An angle γ is a cone angle formed between the guiding blocks 11 on the upper side of the guiding mechanism 1.

In FIG. 2-1 to FIG. 2-2, a rotary structure having a large upper part, a small middle part and a large lower part is formed between the guiding blocks 11, the positioning groove 10 is disposed at the wasp-waist of the guiding block 11, the bottom 32 of the sealing ring 3 is embedded in the positioning groove 10, and the sealing ring 3 surrounds the guiding block 11 from the outside.

After the 12 mm surgical instrument 8 is inserted, the guiding blocks 11 splay outward, gaps 12 between the guiding blocks 11 increase and the sealing ring confined within the positioning groove 10 extends out of the gaps 12 between the guiding blocks to surround the surgical instrument and form sealing.

The length L-SH of the "soft-hard" friction area formed between the silica gel sealing ring and the outer metal sheath of the surgical instrument of the sealing apparatus of the present invention is comparable to the height of the positioning groove 10 after the 12 mm surgical instrument 8 is inserted, thereby greatly reducing the frictional resistance when the surgical instrument moves.

FIG. 2-3 is a side view of FIG. 2-1.

FIG. 2-4 is a schematic three-dimensional structural diagram of a guiding mechanism in the upper part of FIG. 2-3.

FIG. 2-5 is a schematic three-dimensional structural diagram of the guiding mechanism in the lower part of FIG. 2-3.

FIG. 2-6 is a schematic structural diagram of a guiding block.

FIG. 2-7 is a schematic structural diagram of the side face of the guiding block.

FIG. 2-8 is a schematic diagram of the position between each guiding block forming the guiding mechanism.

FIG. 2-9 is an exploded view of FIG. 2-3.

FIG. 3-1 is a schematic structural diagram of a sealing apparatus having a wedge-shaped positioning groove according to the present invention.

Figure 31:
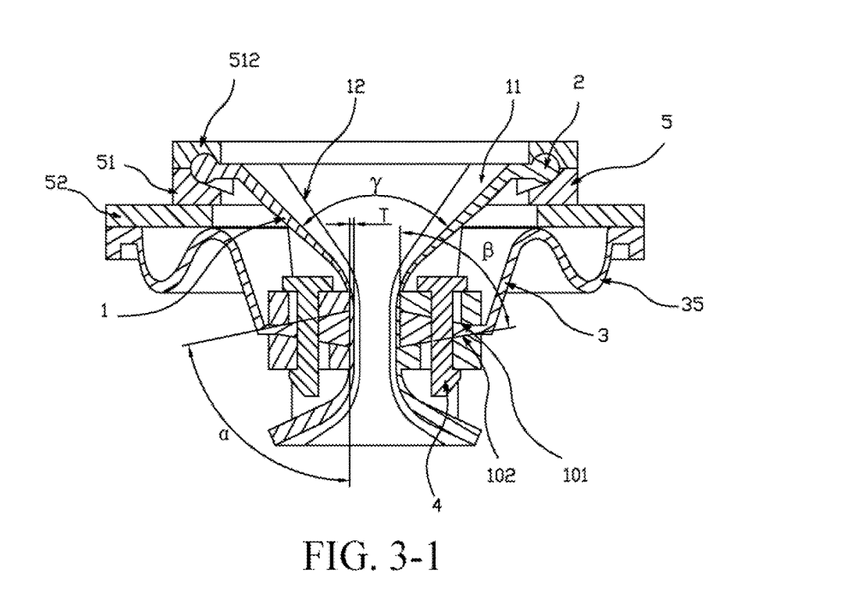
Figure 32:
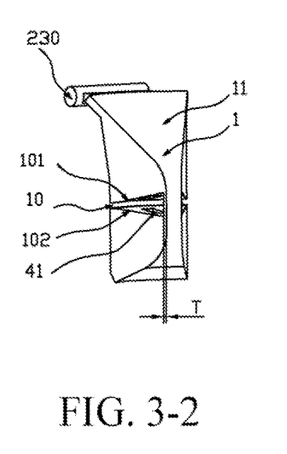
Figure 33:
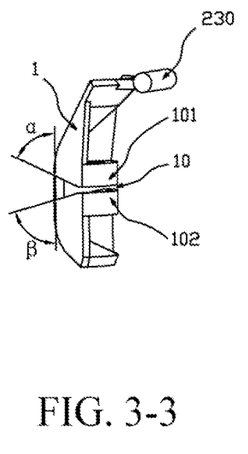
Figure 34:
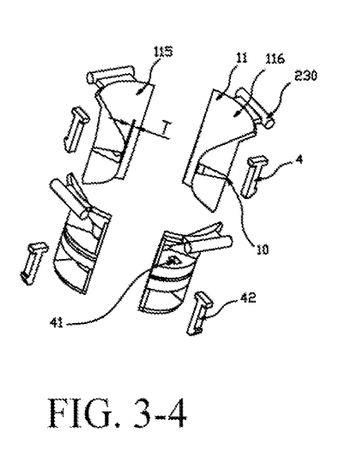

In FIG. 3-1, an angle α is the angle between an upper edge 101 of the positioning groove and the vertical base of the positioning groove, and an angle β is the angle between a lower edge 102 of the positioning groove 10 and the vertical base of the positioning groove. T is the thickness between the front end of the positioning groove 10 and the guiding surface at the wasp-waist of the guiding block 11. The smaller the thickness T is, the softer the material is, the better the fitting with the outer wall of a surgical instrument is, the stronger the surrounding capability for the surgical instrument formed after the sealing ring 3 extends out of the gap 12 is, and also the better the sealing capability is. The clinical applications have shown that the ring sealing apparatus of the present invention can completely satisfy the requirement of maintaining pneumoperitoneum pressure in a laparoscopic surgery. According to the difference of materials of the guiding block 11, the thickness T is between 0.01 mm and 2 mm, and preferably between 0.05 mm and 1 mm. The guiding block 11 is preferably made of a material having good flexibility, such as medical PP, medical PU and medical PTEF. The thickness T may be controlled between 0.05 mm and 0.15 mm, so that the wasp-waist of the guiding block 11 and the silica gel sealing ring extending out of the gaps 12 have excellent surrounding capability for the surgical instrument, thereby obtaining a preferred dynamic sealing effect.

FIG. 3-2 is a schematic structural diagram of a guiding block with a wedge-shaped positioning groove.

FIG. 3-3 is a schematic structural diagram of the side face of the guiding block with a wedge-shaped positioning groove.

FIG. 3-4 is a schematic diagram of the position between different guiding blocks of a guiding mechanism formed by a wedge-shaped positioning groove.

FIG. 4-1 is a schematic structural diagram of a sealing apparatus adopting a dynamic connection mechanism of a groove structure according to the present invention.

FIG. 4-2 is a schematic three-dimensional structural diagram of the upper part of FIG. 4-1.

FIG. 5-1 is a schematic structural diagram of a sealing apparatus adopting a spherical dynamic connection mechanism according to the present invention.

FIG. 5-2 is a schematic diagram of the position between different guiding blocks of the sealing apparatus according to the present invention in FIG. 5-1.

FIG. 6-1 is a schematic structural diagram of a trocar according to the present invention.

FIG. 6-2 is a schematic structural diagram of a sheath of the trocar according to the present invention.

In the foregoing accompanying drawings:

1 is a guiding mechanism, 2 is a dynamic connection mechanism, 3 is a sealing ring, 4 is a connection locking mechanism, 5 is a translation slider mechanism, 6 is a sheath of a trocar, 7 is a sealing apparatus of the present invention, 8 is a surgical instrument or a trocar rod, and 9 is a check valve or an axial sealing apparatus of a trocar.

10 is a positioning groove, 11 is a guiding block, 12 is the gap between guiding blocks, 101 is the upper edge of the positioning groove, 102 is the lower edge of the positioning groove, 115 is a main guiding slider, and 116 is an auxiliary guiding slider.

21 is an elastic low-resistance area, 22 is a ball connection rotation mechanism, 23 is a rotation mechanism of a shaft connection mechanism; 210 is a groove structure of a low-resistance area, 220 is a ball limit slot of a ball connection rotation mechanism, 221 is a ball movable in the ball limit slot, 230 is a shaft limit slot, and 231 is a shaft movable in the shaft limit slot.

31 is a surgical instrument through hole of a sealing ring, 32 is the bottom of the sealing ring, 33 is a through hole of the sealing ring for positioning, and 35 is a low-resistance buffering area easy to deform elasticity.

41 is a pin hole of a connection locking mechanism and 42 is a pin.

51 is an upper horizontal positioning plate, 52 is a lower horizontal positioning plate, 511 is a positioning groove of a dynamic connection mechanism, 512 is a cover plate of the dynamic connection mechanism, and 513 is a fastener of an upper cover.

Angle α is the angle between the upper edge 101 of the positioning groove and the vertical base of the positioning groove;

Angle β is the angle between the lower edge 102 of the positioning groove 10 and the vertical base of the positioning groove;

Angle γ is a cone angle formed between guiding blocks 11 at the upper part of the guiding mechanism 1.

δ is the thickness of the bottom of the sealing ring.

T is the thickness between the front end of the positioning groove 10 and a guiding surface at the wasp-waist of the guiding block 11.

$D_{12}$ is the position of an arc with the diameter being 12 mm, $D_{31}$ is the diameter of the surgical instrument through hole of the sealing ring, and $D_{32}$ is the diameter of the bottom of the sealing ring.

L-SH is the length of a "soft-hard" friction area formed between the silica gel sealing ring and the surgical instrument after a 12 mm surgical instrument is inserted, and L-HH is the length of a "hard-hard" friction area formed between the plastics of an upper guiding surface and an outer metal sheath of the surgical instrument after the 12 mm surgical instrument is inserted.

DETAILED DESCRIPTION

Embodiment 1

A 4-Petal Ring Sealing Apparatus Adopting an Axial Dynamic Connection Mechanism According to the Present Invention Referring to FIG. 2-1 to FIG. 2-9, specific part drawings designed according to technical solutions of the present invention are shown.

A guiding block 11, a connection locking mechanism 4 and a translation slider mechanism 5 are made of medical macromolecular materials including, but not limited to, medical materials such as medical PP, medical PE, medical PU, medical PA, medical PC and medical PTEF. Ultra smooth material coating may be further arranged on the guiding face of the guiding block 11 to reduce the frictional resistance when the surgical instrument moves.

A sealing ring 3 is made of a medical elastic material including, but not limited to, flexible medical materials such as medical silica gel, medical rubber, medical polyurethane and medical latex.

In assembling, the bottom 32 of the sealing ring 3 is embedded in a positioning groove 10 of a guiding mechanism 1 and connects the bottom 32 of the sealing ring, an upper edge 101 and a lower edge 102 of the positioning groove fixedly through a connection locking mechanism 4, thereby forming a sealing structure.

In this embodiment, a rotary structure having a large upper part, a small middle part and a large lower part is formed between the guiding blocks 11, the positioning groove 10 is disposed at the wasp-waist of the guiding block 11, and the bottom 32 of the sealing ring 3 surrounds the positioning groove 10 of the guiding block 11 from the outside.

Figure 29:
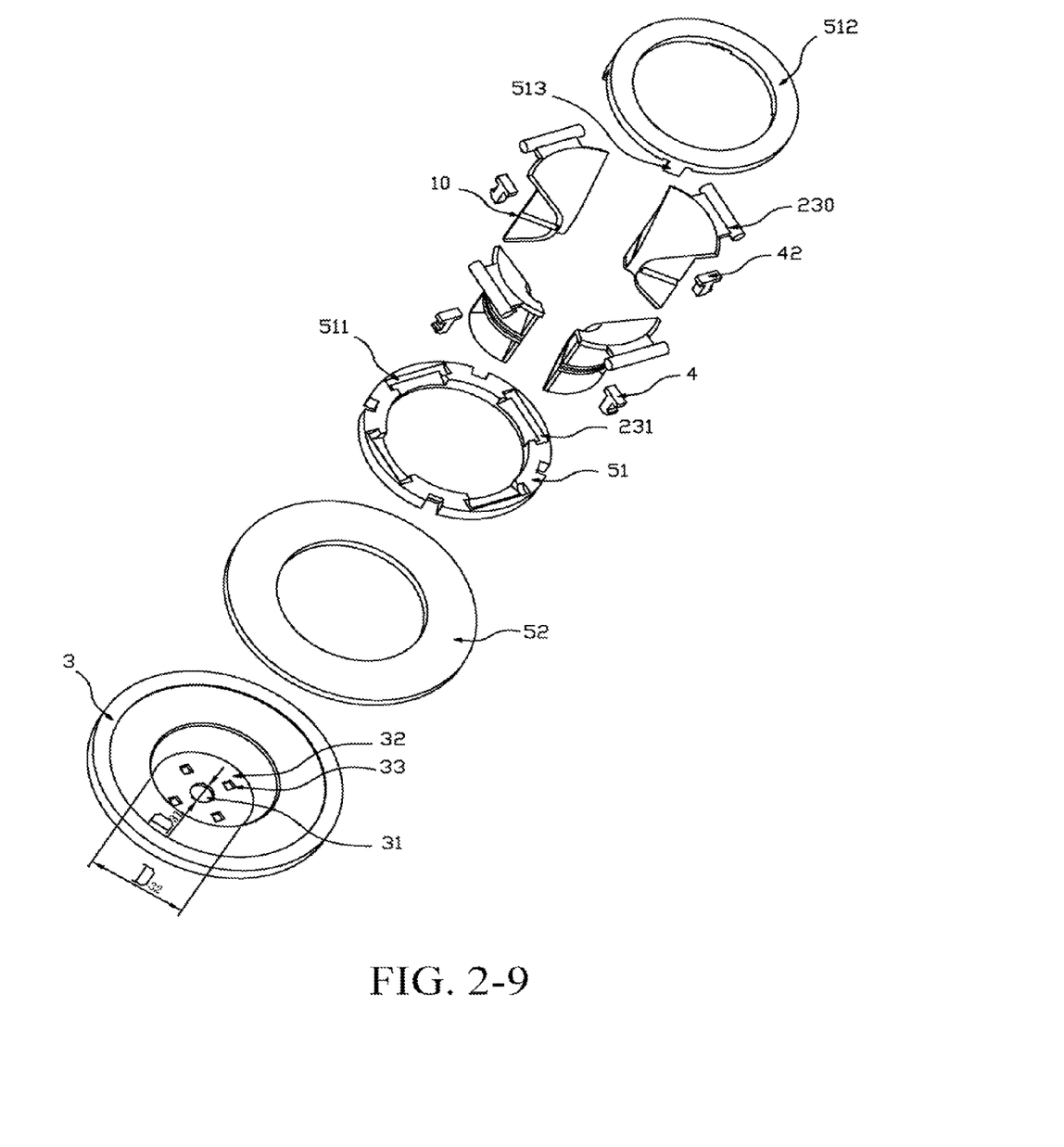

A dynamic connection mechanism 2 of the guiding mechanism 1 is implemented through a shaft connection rotation mechanism 23 disposed on a translation slider mechanism 5. A horizontal slider 51 of the translation slider mechanism 5 may perform 2-dimensional relative motion along the horizontal plane on the horizontal positioning plate 52, namely, the translation slider mechanism 5 may adjust the position of the central axis of the rotary structure formed between the guiding blocks 11.

The shaft 231 is movably mounted in a shaft limit slot 230. When a surgical instrument 8 is inserted, the shaft 231 may rotate in the clockwise direction, the guiding blocks 11 of the guiding mechanism 1 splay outward, a gap 12 between the guiding blocks 11 increases, the diameter of the surgical instrument through hole 31 of the sealing ring 3 also increases, thereby facilitating the inserting of the surgical instrument. Meanwhile, the sealing ring 3 confined within the positioning groove 10 extends out of the gap 12 between the guiding blocks, and surrounds the outer metal sheath of the surgical instrument, together with a thin wall formed in the positioning groove 10 of the wasp-waist of the guiding block 11, thereby forming sealing.

Here, the thickness of the thin wall between the front end of the positioning groove 10 and the guiding surface at the wasp-waist of the guiding block 11 is T. The smaller the thickness T is and the softer the material is, the better the fitting with an outer wall of the surgical instrument is. After extending out of the gap 12, the sealing ring 3 surrounds of the surgical instrument together with the thin wall between the guiding surfaces at the wasp-waist of the guiding block 11. The smaller the thickness T is and the softer the extended sealing ring is, the better the fitting with the outer sheath of the surgical instrument is, and the stronger the sealing capability is.

The clinical applications have shown that the ring sealing apparatus of the present invention can completely satisfy the requirement of maintaining pneumoperitoneum pressure in a laparoscopic surgery. According to the difference of the materials fabricating the guiding block 11, the thickness T is between 0.01 mm and 2 mm, and preferably between 0.05 mm and 1 mm. The guiding block 11 is preferably made of a material with good flexibility, such as medical PP, medical PU and medical PTEF. The thickness T can be controlled between 0.05 mm and 0.15 mm, so that the wasp-waist of the guiding block 11 and the silica gel sealing ring extending out of the gap 12 have excellent surrounding capability for the surgical instrument, thereby obtaining a preferred dynamic sealing effect.

When the surgical instrument 8 is removed, the guiding surface on the lower side of the guiding mechanism 1 has a guiding effect to facilitate the removing of the surgical instrument, and under the effect of elastic resilience of the sealing ring 3, the guiding blocks 11 contract inward, the shaft 231 rotates in the anticlockwise direction, the gap 12 between the guiding blocks 11 decreases, the guiding blocks 11 and the sealing ring 3 restore to the initial state without the inserting of the surgical instrument, namely, the surgical instrument through hole 31 of the sealing ring restores to the initial diameter. Meanwhile, the guiding blocks 11 also restore to the initial position without the inserting of the surgical instrument, namely, a rotary structure having a large upper part, a small middle part and a large lower part is formed between the guiding blocks 11.

By means of the design of the present invention, no matter the surgical instrument is inserted or removed, the motion resistance of the surgical instrument is mainly "hard-hard" friction between the outer metal sheath of the surgical instrument and the plastic guiding surface of the guiding block 11. The "soft-hard" friction area between the sealing ring 3 and the outer metal sheath of the surgical instrument is a "soft-hard" friction area formed between the sealing ring 3 extending out of the gap 12 and the outer metal sheath of the surgical instrument. The length L-SH of the "soft-hard" friction area is comparable to the height of the positioning groove 10, thereby greatly reducing the "soft-hard" friction area, and implementing low resistance when the surgical instrument moves.

In this embodiment, a cone angle γ formed between the guiding blocks 11 of the upper part of the guiding mechanism 1 is between 180° and 20°, and optimally between 100° and 30°.

Additionally, the lower guiding part of the guiding mechanism 1 of the sealing apparatus of the present invention not only has a guiding function, but also has the effect of preventing turnover of the sealing ring when the surgical instrument is withdrawn outward. The turnover of the sealing ring greatly increases the resistance when the surgical instrument is withdrawn. The sealing apparatus of the present invention avoids the turnover phenomenon.

By means of the sealing apparatus of the present invention, surgical instruments with diameters between 5 mm and 12 mm can be freely inserted, while maintaining excellent dynamic sealing performance. The sealing apparatus and the trocar of the present invention can further implement free changing of surgical instruments with diameters between 5 mm and 15 mm, while maintaining low motion resistance.

In this embodiment, the upper edge 101 of the positioning groove and the lower edge 102 of the positioning groove may further be connected together fixedly through a heat seal process or through binding by using a chemical binder. After passing through the bottom 32 of the silicone rubber sealing ring 3, a raised pin 42 is inserted into a pin hole 41 to form concave-convex matching. In this area, an ultrasonic wave heat seal process may be adopted to connect the upper edge 101 of the positioning groove and the lower edge 102 of the positioning groove together fixedly. Another method is that the chemical binder may be used at the concave-convex matching area to bind the upper edge 101 of the positioning groove and the lower edge 102 of the positioning groove together fixedly.

Embodiment 2

A Sealing Apparatus Adopting a Wedge-Shaped Positioning Groove According to the Present Invention Referring to FIG. 3-1 to FIG. 3-4, technical principles of this embodiment are similar to those in Embodiment 1, and the difference only lies in that: the positioning groove 10 adopts a wedge-shaped structure. The objective of using a wedge-shaped slot is: when a connection locking mechanism 4 is used to compress and fix the sealing ring to form a sealing structure, because of the pressure of the upper and lower bevel edges, the sealing ring is pressed from the outside, thereby enhancing the surrounding force of the sealing ring 3 for a surgical instrument 8.

In this embodiment, the angle α between an upper edge 101 of the positioning groove 10 and the vertical base of the positioning groove is between 90° and 30°, and optimally between 87° and 45°; and the angle β between the lower edge 102 of the positioning groove 10 and the vertical base of the positioning groove is between 90° and 30°, and optimally between 87° and 45°.

Embodiment 3

Figure 41:
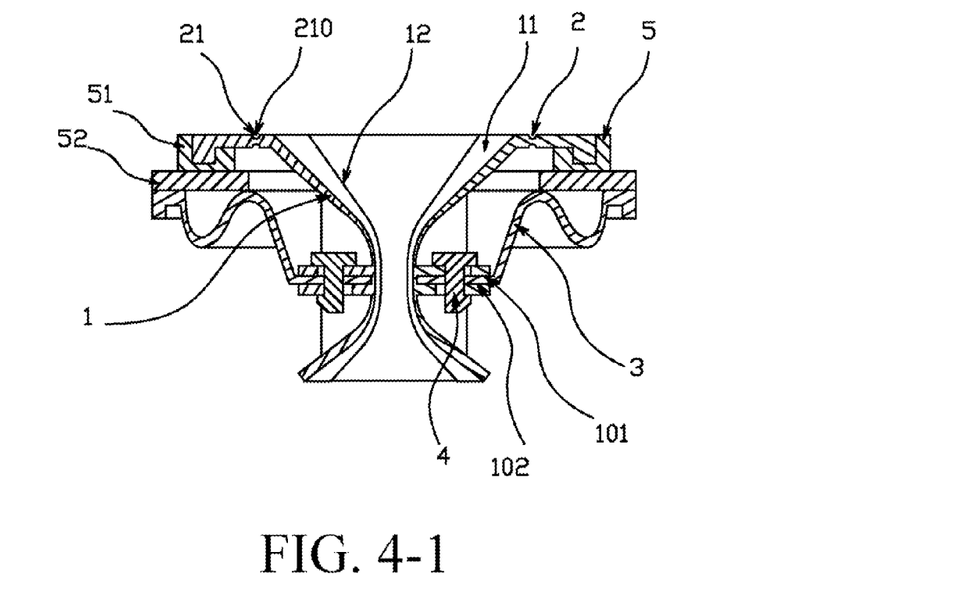
Figure 42:
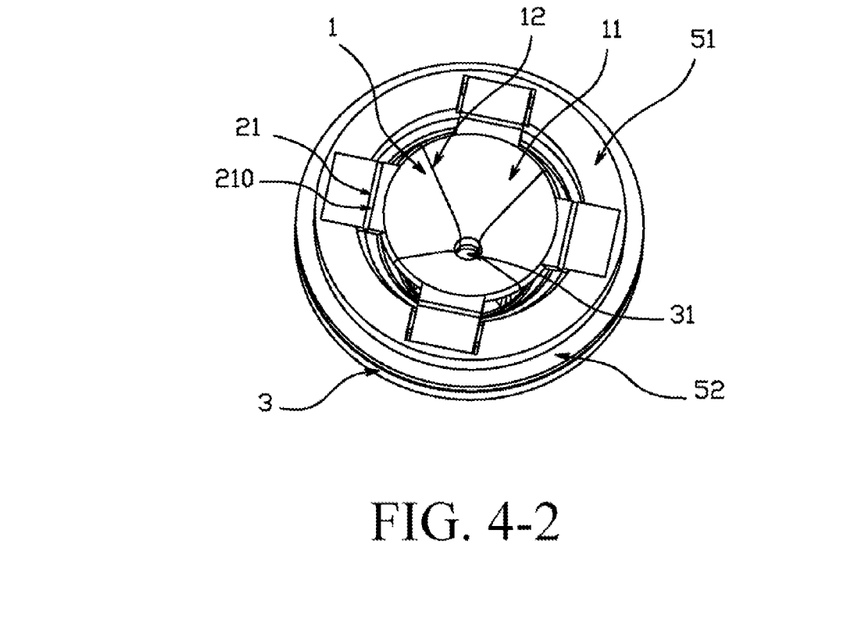

A Sealing Apparatus Adopting a Groove Type Dynamic Connection Mechanism According to the Present Invention Referring to FIG. 4-1 to FIG. 4-2, the difference of this embodiment from Embodiment 1 lies in that: the dynamic connection mechanism of Embodiment 1 adopts an axial connection mechanism, while in this embodiment, an elastic low-resistance area 21 is formed through a groove 210, so as to serve as a dynamic connection structure 2.

When the surgical instrument 8 is inserted, the groove 210 deforms and drives guiding blocks 11 and a sealing ring 3 to splay outward, a gap 12 increases, the pressed sealing ring 3 extends out of the increased gap to surround an outer sheath of the surgical instrument, thereby having a sealing effect.

When the surgical instrument 8 is removed, a guiding surface on the lower side of the guiding block 11 has the guiding effect, thereby facilitating the removing of the surgical instrument. Under the effect of the elastic resilience of the sealing ring 3, the sealing ring 3 restores to an initial state without the inserting of the surgical instrument, namely, a surgical instrument through hole 31 of the sealing ring restores to the initial diameter, and meanwhile, the guiding blocks 11 also restore to the initial position without the inserting of the surgical instrument.

Embodiment 4

Figure 51:
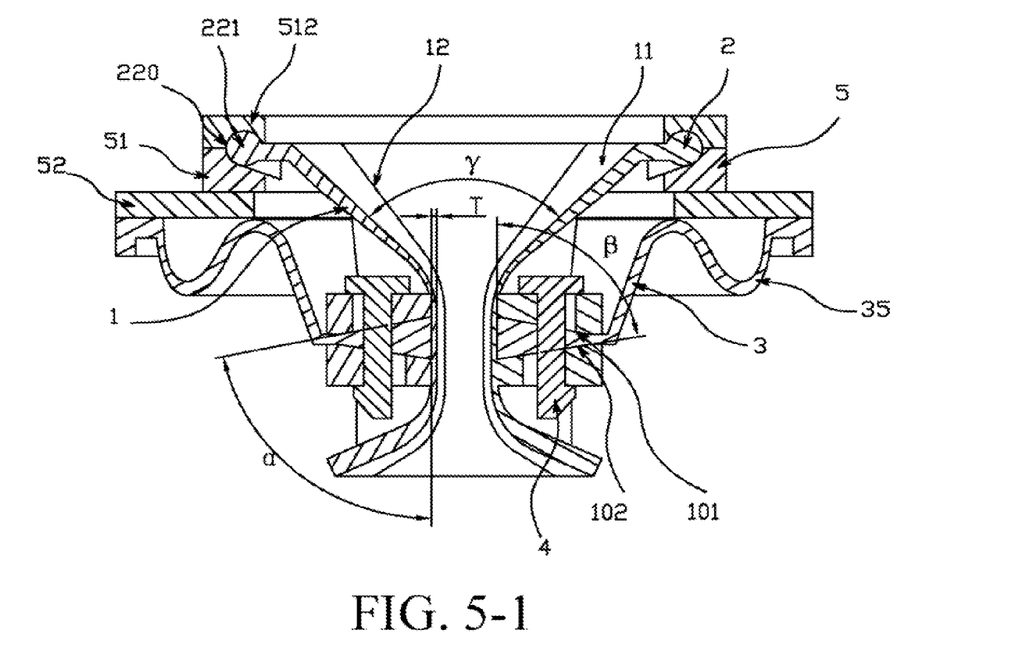
Figure 52:
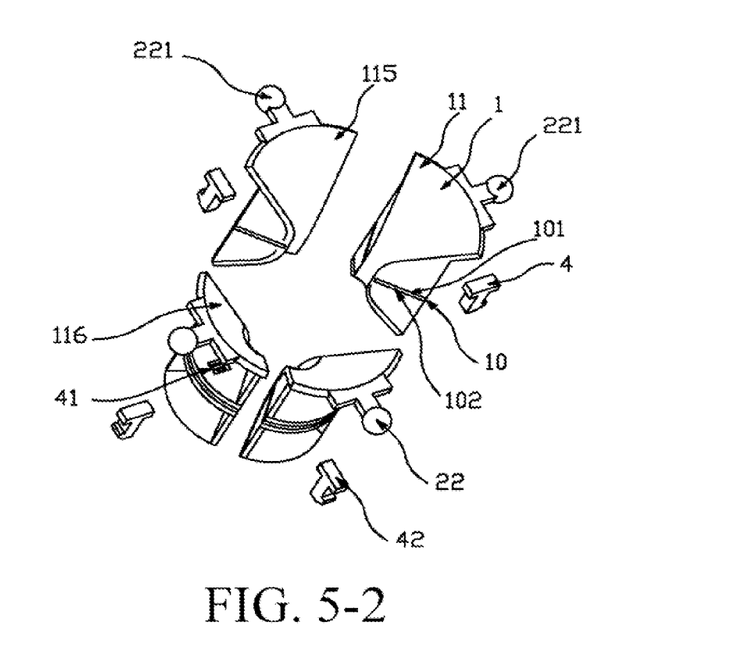

A Sealing Apparatus of a Spherical Dynamic Connection Mechanism of the Present Invention Referring to FIG. 5-1 to FIG. 5-2, the difference of this embodiment from Embodiment 1 lies in that: in Embodiment 1, the dynamic connection mechanism adopts an axial connection mechanism, while this embodiment, a spherical connection mechanism is adopted as a dynamic connection structure 2. A ball 221 is mounted in a spherical limit slot 220 of the ball connection mechanism, and the ball 221 may perform relative motion in the spherical limit slot 220.

When the surgical instrument 8 is inserted, guiding blocks 11 and a sealing ring 3 splay outward, a gap 12 increases, the pressed sealing ring 3 extends out through the increased gap to surround an outer sheath of the surgical instrument, thereby having the sealing effect.

When the surgical instrument 8 is removed, a guiding surface on the lower side of the guiding block 11 has the guiding effect, thereby facilitating the removing of the surgical instrument. Under the effect of the elastic resilience of the sealing ring 3, the sealing ring 3 restores to the initial state without the inserting of the surgical instrument, namely, a surgical instrument through hole 31 of the sealing ring restores to the initial diameter. Meanwhile, the guiding blocks 11 also restore to the initial position without the inserting of the surgical instrument.

Embodiment 5

A Trocar According to the Present Invention

Figure 61:
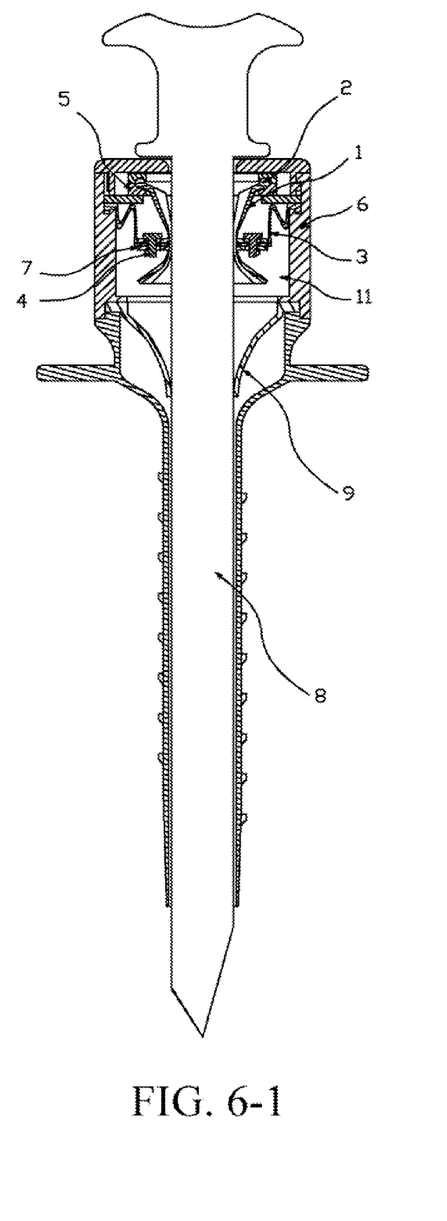
Figure 62:
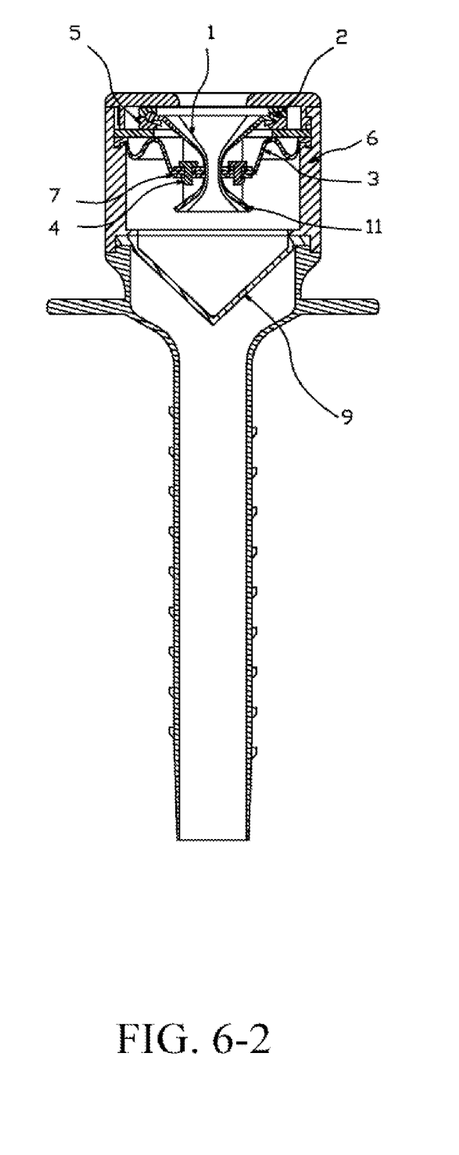

Referring to FIG. 6-1 to FIG. 6-2, in this embodiment, the radial sealing adopts the ring sealing apparatus of the present invention, while the axial sealing, namely, a check valve 9, adopts a silicone rubber straight sealing ring.

In this embodiment, a rotary structure having a large upper part, a small middle part and a large lower part is formed between guiding blocks 11, a positioning groove 10 is disposed at the wasp-waist of the guiding block 11, and the bottom 32 of a sealing ring 3 surrounds the positioning groove 10 of the guiding block 11 from the outside.

A dynamic connection mechanism 2 of a guiding mechanism 1 is implemented through a shaft connection rotation mechanism 23 disposed on a translation slider mechanism 5. A horizontal slider 51 on the translation slider mechanism 5 may perform 2-dimensional relative motion along the horizontal plane on the horizontal positioning plate 52, namely, the translation slider mechanism 5 may adjust the position of the central axis in the rotary structure formed between the guiding blocks 11.

A shaft 231 is movably mounted in a shaft limit slot 230. When a surgical instrument 8 is inserted, the shaft 231 may rotate in the clockwise direction, the guiding blocks 11 of the guiding mechanism 1 splay outward, a gap 12 between the guiding blocks 11 increases, and the diameter of a surgical instrument through hole 31 of the sealing ring 3 also increases, thereby facilitating the inserting of the surgical instrument. Meanwhile, the pressed sealing ring 3 in the positioning groove 10 extends out of the gap 12 between the guiding blocks and surrounds an outer metal sheath of the surgical instrument together with a thin wall formed in the positioning groove 10 at the wasp-waist of the guiding block 11, thereby forming sealing.

Here, the thickness of the thin wall between the front end of the positioning groove 10 and the guiding surface at the wasp-waist of the guiding block 11 is T. The smaller the thickness T is and the softer the material is, the better the fitting with the outer wall of the surgical instrument is. After extending out of the gap 12, the sealing ring 3 surrounds the surgical instrument together with the thin wall between the guiding surfaces at the wasp-waist of the guiding block 11. The smaller the thickness T is and the softer the extended sealing ring is, the better the fitting with the outer sheath of the surgical instrument is and the stronger the sealing capability is.

The clinical applications have shown that the ring sealing apparatus of the present invention can completely satisfy the requirement of maintaining pneumoperitoneum pressure in a laparoscopic surgery. According to the difference of the materials fabricating the guiding block 11, the thickness T is between 0.01 mm and 2 mm, and preferably between 0.05 mm and 1 mm. The guiding block 11 is preferably made of a material with good flexibility, such as medical PP, medical PU and medical PTEF. The thickness T can be controlled between 0.05 mm and 0.15 mm, so that the wasp-waist of the guiding block 11 and the silica gel sealing ring extending out of the gap 12 have excellent surrounding capability for the surgical instrument, thereby obtaining a preferred dynamic sealing effect.

When the surgical instrument 8 is removed, the guiding surface on the lower part of the guiding mechanism 1 has a guiding effect and facilitates the removing of the surgical instrument, and under the effect of the elastic resilience of the sealing ring 3, the guiding blocks 11 contract inward, the shaft 231 rotates in the anticlockwise direction, the gap 12 between the guiding blocks 11 decreases, and the guiding blocks 11 and the sealing ring 3 restore to the initial state without the inserting of the surgical instrument, namely, the surgical instrument through hole 31 of the sealing ring restores to the initial diameter. Meanwhile, the guiding blocks 11 also restore to the initial position without the inserting of the surgical instrument, namely, a rotary structure having a large upper part, a small middle part and a large lower part is formed between the guiding blocks 11.

By means of the design of the present invention, no matter the surgical instrument is inserted or removed, the motion resistance of the surgical instrument is mainly "hard-hard" friction between the outer metal sheath of the surgical instrument and the plastic guiding surface of the guiding block 11. The "soft-hard" friction area between the sealing ring 3 and the outer metal sheath of the surgical instrument is a "soft-hard" friction area formed between the sealing ring 3 extending out of the gap 12 and the outer metal sheath of the surgical instrument. The length L-SH of the "soft-hard" friction area is comparable to the height of the positioning groove 10, thereby greatly reducing the "soft-hard" friction area, and implementing low resistance when the surgical instrument moves.

Additionally, the radial sealing apparatus for the trocar according to the present invention may adopt the ring sealing apparatus of the present invention, and the axial sealing apparatus, namely, the check valve 9 adopts a flipping-type sealing apparatus. For the trocar adopting the combination according to the present invention, when no surgical instrument is inserted, a spring of the flipping-type sealing apparatus oppresses the silica gel sealing ring of the flipping-type sealing apparatus to prevent leakage of $CO_2$ gas.

When the surgical instrument is inserted, the surgical instrument 8 enters along a guiding mechanism 1, the guiding blocks 11 splay outward, the gap 12 between the guiding blocks 11 gradually increases and the lower part of the sealing ring 3 deforms, while the surgical instrument through hole 31 of the sealing ring surrounds the surgical instrument 8 to form radial sealing. Meanwhile, the flipper is pushed open by the surgical instrument, so the surgical instrument can be inserted in a body cavity.

When the surgical instrument is removed, the surgical instrument 8 is gradually removed along the guiding mechanism 1. Under the effect of the elastic resilience of the sealing ring 3, the guiding blocks 11 gradually contract centripetally, and the gap 12 gradually reduces. When the surgical instrument is completely removed, the surgical instrument through hole 31 of the sealing ring completely restores to the initial state. Meanwhile, the spring of the flipping-type sealing apparatus oppresses the silica gel sealing ring of the flipping-type sealing apparatus and again closes the axial check valve to prevent leakage of $CO_2$ gas.

The radial sealing apparatus for the trocar according to the present invention may adopt the ring sealing apparatus of the present invention, and the axial sealing apparatus, namely, the check valve 9, adopts a spherical sealing apparatus.

It should be pointed out that, a magnet can be mounted in the guiding mechanism 1 of the sealing apparatus of the present invention and a hollow sphere can be made of a ferromagnetic material. Under the attraction of the magnetic force, the sphere and the surgical instrument through hole 31 of the sealing ring of the sealing apparatus of present invention form axial sealing, namely, the check valve 9.

When the surgical instrument is inserted, the surgical instrument 8 enters along the guiding mechanism 1, the guiding blocks 11 splay outward, the gap 12 between the guiding blocks 11 gradually increases, and the lower part of the sealing ring 3 deforms, while the surgical instrument through hole 31 of the sealing ring surrounds the surgical instrument 8 to form radial sealing. Meanwhile, the hollow sphere is pushed open by the surgical instrument, so the surgical instrument can be inserted in a body cavity.

When the surgical instrument is removed, the surgical instrument 8 gradually removes along the guiding mechanism 1, and under the effect of elastic resilience of the sealing ring 3, the guiding blocks 11 gradually contract centripetally, and the gap 12 gradually reduces. When the surgical instrument is completely removed, the surgical instrument through hole 31 of the sealing ring completely restores to the initial state. Meanwhile, under the effect of magnetic force, the hollow sphere blocks the surgical instrument through hole 31 of the sealing ring, thereby having an axial sealing effect and preventing leakage of $CO_2$ gas.

Additionally, a trocar rod used by the trocar of the present invention may be a trocar rod with a protection cutterhead, or may be a trocar rod without a protection cutterhead, such as a triangular blade trocar rod, a conical blunt trocar rod, and a blunt trocar rod with flanks.

It should be noted that, the structures disclosed and illustrated in the specification may be replaced by other structures with same effect, and meanwhile, the embodiments introduced in the present invention are not the unique structure implementing the present invention. Although preferred embodiments of the present invention are already introduced and illustrated in the specification, but it is clearly known by persons of skill in the art that the embodiments are merely examples, and persons of skill in the art can make innumerable change, improvement and replacement without departing from the present invention. Therefore, the protection scope of the present invention shall be limited according to the spirit and scope of claims accompanied by the present invention.

While particular embodiments are described above, it will be understood it is not intended to limit the present invention to these particular embodiments. On the contrary, the present invention includes alternatives, modifications and equivalents that are within the spirit and scope of the appended claims. Numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the embodiments.

Although the terms first, second, etc. may be used herein to describe various elements, these elements should not be limited by these terms. These terms are only used to distinguish one element from another. For example, first ranking criteria could be termed second ranking criteria, and, similarly, second ranking criteria could be termed first ranking criteria, without departing from the scope of the present invention. First ranking criteria and second ranking criteria are both ranking criteria, but they are not the same ranking criteria.

The terminology used in the description of the present invention herein is for the purpose of describing particular embodiments only and is not intended to be limiting of the present invention. As used in the description of the present invention and the appended claims, the singular forms "a," "an," and "the" are intended to include the plural forms as well, unless the context clearly denotes otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, operations, elements, and/or components, but do not preclude the presence or addition of one or more other features, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

Although some of the various drawings illustrate a number of logical stages in a particular order, stages that are not order dependent may be reordered and other stages may be combined or broken out. While some reordering or other groupings are specifically mentioned, others will be obvious to those of ordinary skill in the art and so do not present an exhaustive list of alternatives. Moreover, it should be recognized that the stages could be implemented in hardware, firmware, software or any combination thereof.

The foregoing description, for purpose of explanation, has been described with reference to specific implementations. However, the illustrative discussions above are not intended to be exhaustive or to limit the present invention to the precise forms disclosed. Many modifications and variations are possible in view of the above teachings. The implementations were chosen and described in order to best explain principles of the present invention and its practical applications, to thereby enable others skilled in the art to best utilize the present invention and various implementations with various modifications as are suited to the particular use contemplated. Implementations include alternatives, modifications and equivalents that are within the spirit and scope of the appended claims. Numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the implementations.

What is claimed is:

1. A ring sealing apparatus for a trocar, comprising a guiding mechanism and a sealing ring, wherein
the guiding mechanism comprises a positioning groove for mounting the sealing ring and four guiding blocks including two guiding blocks of a large guiding surface forming a pair of primary guiding sliders and two guiding blocks of a small guiding surface forming a pair of auxiliary guiding sliders, wherein the primary guide sliders and the auxiliary guiding sliders have different colors;
the four guiding blocks form a rotary structure having a large upper part, a small middle part and a large lower part; and the positioning groove is disposed at the small middle part of the guiding block;
the sealing ring is made of an elastic medical macromolecular material, and has a surgical instrument through hole; and
the sealing ring is mounted in the positioning groove.

2. The ring sealing apparatus for a trocar according to claim 1, wherein the bottom of the sealing ring close to the surgical instrument through hole is placed between an upper edge and a lower edge of the positioning groove, forming a sealing structure by being fixed together with the positioning groove through a connection locking mechanism.

3. The ring sealing apparatus for a trocar according to claim 2, wherein an angle α between the upper edge of the positioning groove and the vertical base of the positioning groove is between 90° and 30°; and an angle β between the lower edge of the positioning groove and the vertical base of the positioning groove is between 90° and 30°.

4. The ring sealing apparatus for a trocar according to claim 1, wherein a cone angle γ formed by the large upper part and the small middle part of the guiding blocks is between 180° and 20°.

5. The ring sealing apparatus for a trocar according to claim 1, wherein the upper part of the sealing ring close to its edge comprises a low-resistance buffering area that easily deforms elastically.

6. The ring sealing apparatus for a trocar according to claim 5, wherein the low-resistance buffer area of the sealing ring adopts a wrinkle structure.

7. The ring sealing apparatus for a trocar according to claim 1, wherein the sealing ring is a sealing ring having one selected from the group consisting of a trapezoidal, V-shaped or H-shaped cross section.

8. The ring sealing apparatus for a trocar according to claim 7, wherein the sealing ring is a sealing ring having a trapezoidal cross section, the diameter $D_{31}$ of the surgical instrument through hole is between 1 mm and 5 mm; the diameter $D_{32}$ of the bottom of the trapezoidal sealing ring is between 3 mm and 40 mm; and the thickness δ of the bottom of the trapezoidal sealing ring is between 0.05 mm and 5 mm.

9. The ring sealing apparatus for a trocar according to claim 1, wherein the sealing apparatus comprises a dynamic connection mechanism.

10. The ring sealing apparatus for a trocar according to claim 9, wherein the dynamic connection mechanism refers to an elastic low-resistance area that is formed of elastic materials, easily deforms under an external force and restores its shape after the external force of deformation is removed; or, the dynamic connection mechanism refers to a movable ball connection rotation mechanism or a shaft connection rotation mechanism.

11. The ring sealing apparatus for a trocar according to claim 10, wherein the low-resistance area is a groove structure having a variable thickness.

12. The ring sealing apparatus for a trocar according to claim 10, wherein the ball connection rotation mechanism comprises a ball limit slot and a ball movable in the ball limit slot, and the ball is mounted in the ball limit slot movably.

13. The ring sealing apparatus for a trocar according to claim 10, wherein the shaft connection rotation mechanism comprises a shaft limit slot and a shaft movable in the shaft limit slot, and the shaft is mounted in the shaft limit slot movably.

14. The ring sealing apparatus for a trocar according to claim 9, wherein the horizontal slider comprises a positioning groove mounted with the dynamic connection mechanism, a cover plate, and a fastener.

15. The ring sealing apparatus for a trocar according to claim 1, wherein the sealing apparatus comprises a translation slider mechanism.

16. The ring sealing apparatus for a trocar according to claim 15, wherein the translation slider mechanism comprises a horizontal slider and a horizontal positioning plate, and the horizontal slider movable in the horizontal direction is placed on the horizontal positioning plate.

17. A trocar, comprising the ring sealing apparatus for a trocar according to claim 1 and an axial sealing apparatus.

18. The trocar according to claim 17, wherein the ring sealing apparatus for a trocar is mounted in a sheath of the trocar.

19. The trocar according to claim 17, wherein the axial sealing apparatus adopts a funnel-shaped straight sealing ring.

20. The trocar according to claim 17, wherein the axial sealing apparatus adopts a flipping-type sealing apparatus.

21. The trocar according to claim 17, wherein the axial sealing apparatus adopts a spherical sealing apparatus.

* * * * *